United States Patent [19]

Rosenbrook, Jr.

[11] 4,230,848
[45] Oct. 28, 1980

[54] PROCESS FOR PRODUCING 3-O-DEMETHYLFORTIMICINS

[75] Inventor: William Rosenbrook, Jr., Libertyville, Ill.

[73] Assignee: Abbott Laboratories, North Chicago, Ill.

[21] Appl. No.: 25,238

[22] Filed: Mar. 29, 1979

[51] Int. Cl.$^2$ ............................................. C07H 15/22
[52] U.S. Cl. .................................. 536/17 R; 536/18; 424/180
[58] Field of Search ......................... 536/17 R, 120, 1; 568/907

[56] References Cited

U.S. PATENT DOCUMENTS 4,124,756  11/1978  Martin et al. ........................... 536/17

OTHER PUBLICATIONS

Pigman, "The Carbohydrates", 1957, Academic Press, Inc., New York, N.Y., p. 368.
Noller, "Chemistry of Organic Compounds", 1965, W. B. Saunders Co., Philadelphia, Pa., pp. 161, 395 and 846.

Primary Examiner—JohnnieR. Brown
Attorney, Agent, or Firm—Gildo E. Fato; Joyce R. Niblack; Robert L. Niblack

[57] ABSTRACT

An improved process for producing 3-O-demethylfortimicins comprising the steps of reacting the fortimicin to be 3-O-demethylated with a borontrihalide and recovering the 3-O-demethylfortimicin from the reaction mixture.

12 Claims, No Drawings

PROCESS FOR PRODUCING 3-O-DEMETHYLFORTIMICINS

BACKGROUND OF THE INVENTION

The aminoglycoside antibiotics are a valuable therapeutic class of antibiotics which include the kanamycins, gentamicins, streptomycins and the more recently discovered fortimicins. While the naturally produced parent antibiotics are, in themselves, valuable entities, chemical modifications have been found to improve the activity, either intrinsic or activity against resistant strains, or reduce the toxicity of the parent antibiotics. And, because of the development of aminoglycoside resistant strains and inactivation of the parent antibiotics by R- mediated factors which can develop, the search for new entities continues.

One such entity has been discovered in the fortimicin family of antibiotics, 3-O-demethylfortimicin A. The corresponding 3-O-demethylfortimicin B is also of interest. The 3-O-demethylfortimicins are disclosed in U.S. Pat. No. 4,124,756, issued Nov. 7, 1978.

Previously known methods for producing 3-O-demethylfortimicin A and 3-O-demethylfortimicin B have resulted in such low yields that production of these antibiotics was extremely slow and inefficient, and there has been a need for methods which produce the 3-O-demethylfortimicins in greater yield. The present invention provides one such method.

SUMMARY

The present invention provides an improved process for synthesizing 3-O-demethylfortimicins directly from the parent antibiotics and comprises the steps of reacting the fortimicin to be O-demethylated with a boron trihalide, preferably boron tribromide, preferably in the presence of an inert solvent, i.e., a chlorinated hydrocarbon or hydrocarbon solvent such as methylene chloride which provides solubility for the fortimicins, removal of the solvent and residual boron trihalide and isolation of the desired product by chromatography.

DETAILED DESCRIPTION OF PREFERRED EMBODIMENTS

For illustrative purposes, ths invention will be exemplified by the O-demethylation of fortimicin A and fortimicin B. Generally speaking, in the practice of the preferred embodiment of this invention, to obtain a 3-O-demethylfortimicin, for example 3-O-demethylfortimicin A, in approximately thirty percent yield, fortimicin A free base is dissolved in methylene chloride, preferably in an amount of from about 1.0 to about 100 mg (0.0025 to 0.25 mmole) of fortimicin A free base to each ml of an inert solvent such as methylene chloride, and the reaction mixture is cooled to a temperature of from about −72° to about 4° C., preferably about 0° C. and treated with from about 10 to about 100 equivalents of a boron trihalide selected from the group consisting of boron tribromide, boron trichloride and boron triiodide with stirring for about 10 to 60 minutes, preferably for about 30 minutes at a temperature of from about −72° to about 4° C., preferably at about 0° C.

Solvent and residual boron trihalide are then removed in vacuo at a temperature of from about 30° to about 60° C., the remaining reaction mixture treated with an appropriate solvent such as methanol to remove any remaining solvent and boron halide and then evaporated to a residue, preferably in vacuo, at a temperature of from about 30° to about 60° C. It is preferred to carry out the latter step twice.

3-O-demethylfortimicin A is then isolated by silica gel chromatography using an appropriate solvent system such as methylene chloride-methanol-concentrated ammonia in a 2:3:1 (v/v/v) ratio to obtain the product as the free base in approximately thirty percent yield.

3-O-demethylfortimicin B or a derivative thereof, which are also useful as intermediates in the synthesis of 4-N-acyl and alkyl-3-O-demethylfortimicin B derivatives, can be prepared by reacting fortimicin free base, or a derivative thereof, with a boron trihalide, preferably boron tribromide following the general procedure outlined above for the corresponding fortimicin A derivative. 3-O-demethylfortimicin B is obtained in approximately forty percent yields by the process of this invention.

While it is preferred to first dissolve the fortimicin compound to be demethylated in an inert solvent, demethylation can be effected by reacting the fortimicin with the boron trihalide neat.

The following reaction schemes summarize the process of the present invention.

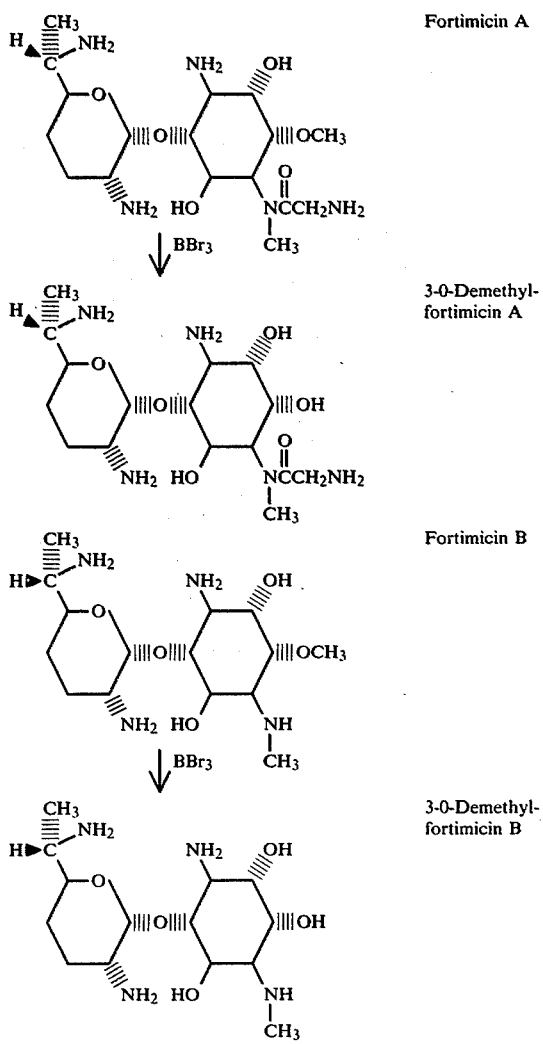

Fortimicin A

3-O-Demethylfortimicin A

Fortimicin B

3-O-Demethylfortimicin B

Fortimicin A can be produced according to the method described in U.S. Pat. No. 3,976,768. Fortimicin B can be prepared according to the method described in U.S. Pat. No. 3,931,400.

The solvents are boron trihalides and other materials used in the practice of this invention and are all available from well known commercial sources.

The following examples further illustrate the present invention.

EXAMPLE 1

3-O-Demethylfortimicin A

Fortimicin A free base (400 mg, 0.99 mmole) was dissolved in dry methylene chloride (25 ml) (distilled from calcium hydride and stored over Type A molecular sieve), cooled to 0° C. and treated with boron tribromide (4.6 ml, 50 mmole). The mixture was stirred under a drying tube for 30 minutes at 0° C. and then for 16 hours at room temperature. Solvent and residual boron tribromide were removed in vacuo at 40° C. in a bath. Methanol (20 ml) was added to the reaction mixture and the mixture was evaporated to a residue in vacuo at 40° C. and the step repeated two times.

3-O-demethylfortimicin A was isolated from the latter residue by silica gel chromatography, using methylene chloride-methanol-concentrated ammonia (2:3:1 v/v/v) is a white foam (116 mg, 30% of theory). Unreacted fortimicin A (164 mg) was also recovered from the chromatography.

EXAMPLE 2

3-O-Demethylfortimicin B

Twenty-five ml of a two percent solution of fortimicin B free base (500 mg, 1.4 mmole) in methylene chloride (stored over Type A molecular sieve) was cooled to 0° C. and treated with boron tribromide (1.3 ml, 3.5 g, 14 mmole). The mixture was stirred under a drying tube for 30 minutes at 0° C. and then for 16 hours at room temperature. Solvent and residual boron tribromide were removed in vacuo at 40° C. (bath). Methanol (20 ml) was added to the reaction mixture and evaporated to a residue in vacuo at 40° C. (bath) and the last step repeated two times.

3-O-Demethylfortimicin B free base (192 mg) was isolated from the latter residue in a 41 percent yield by silica gel column chromatography using methylene chloride-methanol-concentrated ammonia 4:4:1 (v/v/v) as a white foam. This can be converted into the desired salt, as can be product of Example 1, by titration with the appropriate acid. The hydrochloride salt formed by titration with dilute hydrochloric acid and lyophilization of the resulting solution is identical with that described in U.S. Pat. No. 4,124,756.

While the present invention has, for illustrative purposes, been described in connection with the O-demethylation of fortimicin A and fortimicin B, it has successfully been used to O-demethylate known fortimicin A and B derivatives as well as thus to prepare the O-demethyl derivatives directly, including 3-O-demethyl derivatives of U.S. Pat. No. 4,124,756 and of commonly assigned, co-pending U.S. application Ser. No. 863,014, filed Dec. 21, 1977.

I claim:

1. A method of O-demethylating a fortimicin antibiotic comprising the steps of dissolving a fortimicin to be O-demethylated in an inert solvent, cooling the resulting solution to a temperature of from $-72°$ to 4° C., treating said cooled solution with a boron trihalide and thereafter recovering the O-demethylated antibiotic from the reaction mixture.

2. The method of claim 1 wherein said boron trihalide is selected from the group consisting of boron tribromide boron trichloride or boron triiodide.

3. The method of claim 1 wherein the antibiotic to be O-demethylated is reacted as the free base.

4. The method of claim 1 wherein said boron trihalide is selected from the group consisting of boron tribromide, boron trichloride or boron triiodide and the parent antibiotic is reacted as the free base.

5. The method of claim 4 wherein said boron trihalide is boron tribromide.

6. The method of claim 4 wherein said parent antibiotic is fortimicin A free base.

7. The method of claim 4 wherein said parent antibiotic is fortimicin B free base.

8. The method of claim 4 wherein said parent antibiotic is dissolved in a suitable solvent prior to reaction with a boron trihalide to effect 3-O-demethylation.

9. The method of claim 8 wherein said solvent is methylene chloride.

10. The method of claim 9 wherein said boron trihalide is boron tribromide.

11. The method of claim 1 wherein said solution is cooled to a temperature of 0° C. and is reacted with said boron trihalide at about 0° C.

12. The method of claim 4 wherein said solution is cooled to a temperature of 0° C. and is reacted with said boron trihalide at that temperature.

* * * * *